United States Patent [19]

Blumbach et al.

[11] Patent Number: 4,535,156
[45] Date of Patent: Aug. 13, 1985

[54] CHROMOGENIC CEPHALOSPORIN COMPOUND

[75] Inventors: Jürgen Blumbach, Frankfurt am Main; Peter Schindler, Mörfelden-Walldorf, both of Fed. Rep. of Germany

[73] Assignee: Hoechst Aktiengesellschaft, Frankfurt am Main, Fed. Rep. of Germany

[21] Appl. No.: 565,847

[22] Filed: Dec. 29, 1983

Related U.S. Application Data

[63] Continuation of Ser. No. 236,539, Feb. 20, 1981.

[30] Foreign Application Priority Data

Feb. 23, 1980 [DE] Fed. Rep. of Germany ....... 3006889

[51] Int. Cl.$^3$ ................ C07D 501/36; A61K 31/545
[52] U.S. Cl. ......................................... 544/26; 544/22
[58] Field of Search .............. 544/16, 22, 26, 27; 424/246

[56] References Cited

U.S. PATENT DOCUMENTS 3,278,531 10/1966 Cox et al. ..................... 260/243
3,830,700 8/1974 O'Callaghan et al. ........ 195/103.5 R
3,988,326 10/1976 Seki ........................................ 544/29
4,144,392 3/1979 Bradshaw et al. ..................... 544/29

FOREIGN PATENT DOCUMENTS 0018001 10/1980 European Pat. Off. .

Primary Examiner—Nicholas S. Rizzo
Attorney, Agent, or Firm—Curtis, Morris & Safford

[57] ABSTRACT

What are disclosed are cephalosporin derivatives of the formula

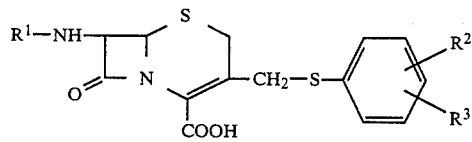

formulations containing such cephem derivatives suitable for the detection of β-lactamases, process for the manufacture of the cephem derivatives and the formulations, and use of the cephem derivatives for the detection of β-lactamases and β-lactamase inhibitors.

1 Claim, No Drawings

CHROMOGENIC CEPHALOSPORIN COMPOUND

This application is a continuation of application Ser. No. 236,539, filed Feb. 20, 1981.

The use of β-lactam antibiotics for the chemotherapy of bacterial infections is restricted by the occurence of β-lactam resistant germs which produce β-lactamases [penicillin-(cephalosporin)-β-lactam-aminohydrolases, EC 3.5.2.6]. These enzymes split the C—N bond of the β-lactam ring, whereby the antibiotic properties of the β-lactams used are lost. To ensure the desired success of the therapy in the treatment of bacterial infections with β-lactam antibiotics prior, to the start of the therapy knowledge is required whether the clinical isolates produce β-lactamases or not. If the β-lactamase test is positive, it is recommended to use β-lactamase resistant β-lactam antibiotics or other antibiotics suitable for clinical use.

To detect germs producing β-lactamase a series of techniques has been described (cf. J. Pharmacol. 15, pages 81 to 91 (1963). The methods are, however, not all fully satisfactory to the extent they involve colorimetric tests, which are especially suitable for clinical-diagnostic purposes, since they all require the addition of an indicator (iodine/starch, hydroxylamine, pH-indicator).

As compared with β-lactamase tests using such indicator coupled test procedures, chromogenic β-lactamase substrates have the advantage that the opening of the β-lactam ring by these enzymes directly results in a color change in the visible part of the spectrum. A chromogenic β-lactamase substrate of this type (compound 87/312) has been described by 0'Callaghan et al.. [Antimicrob.Ag. Chemother. 1, pages 283–288 (1972)]. According to the statements of the authors, however, a bathochromic change of the color of solutions of compound 87/312 takes place not only in the presence of β-lactamases, but also in a non-specific manner after addition of serum, animal tissue, protein, milk, cysteine, glutathione, mercaptoethanol and 2,3-dimercaptopropanol-1. The use of compound 87/312 may lead to a false positive judgement of clinical isolates.

Thus, a feature of the present invention is novel, chromogenic cephalosporins which by a distinctly visible color intensification from a slight yellow to an intense yellow-orange indicate the presence of β-lactamases and which are stable to the aforesaid additives. The β-lactamases can be detected either by means of intact cells of germs which produce β-lactamase or by means of enzymes isolated from these organisms with the aid of standard methods. Besides the mere detection, the compounds according to the invention are well suitable for the determination of the specific activity of isolated β-lactamases.

The compounds of the invention are split by all tested β-lactamases from gram-negative organisms with formation of the above-mentioned color intensification. These are especially β-lactamases of clinically intersting organisms such as *E. coli* R$_{TEM}$, *Klebsiella aerogenes* 1082 E, *Pseudomonas aeruginosa* 18 SH, *Enterobacter cloacae* P 99 and *Bacteroides fragilis* 620. The compounds of the invention are also split by β-lactamases of gram-positive organisms, for example Staphylococcus aureus R 85.

The β-lactamase activity is directly tested with the compounds of the invention, i.e. without coupled test procedures, because the chromophoric substituents of the invention are quantitatively eliminated synchronously with the opening of the β-lactam ring, which directly leads to the color change mentioned above.

It has surprisingly been found that, in contradistinction to β-lactamase substrates of the type 87/312, the compounds of the invention are extremely stable to hydrolytic degradation in a temperature range of from −180° C. to 60° C. in aqueous solutions suitable for the activity of the β-lactamases and the viability of bacteria, but especially in the neutral pH range. Although solutions ready for use are preferably stored at −20° C., at which temperature their stability is practically unlimited, neutrally buffered solutions can be kept at refrigerator temperature for a prolonged period of time and even at room temperature without their usability being impaired.

In addition, the compounds of the invention are completely stable to the influence of serum, protein, milk, cysteine, glutathione, mercaptoethanol and 2,3-dimercaptopropanol-1 (dimercaprol), which constitutes a further surprising advantage over β-lactamase substrates of the type 87/312.

A feature of the present invention are, cephalosporins carrying in 3-position a chromogenic grouping and having the formula I

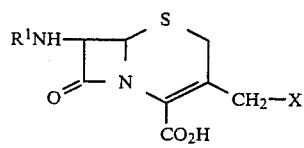

in which $R^1$ is hydrogen, formyl, optionally substituted aroyl or a radical of the formula

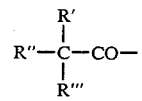

in which R' is hydrogen, optionally substituted alkyl having 1 to 4 carbon atoms, an optionally substituted, saturated or singly or multiply unsaturated carbocyclic ring, optionally substituted aryl or aryloxy, optionally substituted heteroaryl or heteroarylthio, R" and R''', which are identical or different, are hydrogen, alkyl with 1 to 4 carbon atoms, hydroxy, optionally substituted acyloxy, optionally substituted alkoxy, amino, optionally substituted alkylamino, optionally substituted acylamino, alkoxy-carbonyl, halogen, cyano, sulfoxy, or aminosulfonyl, and X is a group of the formula

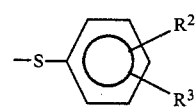

in which $R^2$ means nitro and $R^3$ is hydrogen, nitro, halogen, alkyl, cyano, carboxy, alkoxycarbonyl and aminocarbonyl.

More particularly, in the compound of the invention the substituents are as follows: $R^1$ meaning optionally substituted aroyl can especially stand for benzoyl which may optionally be substituted, for example by alkyl with 1 to 4 carbon atoms, preferably methyl, such as toluoyl, by halogen, preferably chlorine, such as p-chlorobenzoyl, by a nitro group, such as p-nitrobenzoyl, by an amino group, such as p-aminobenzoyl or by an acetamido group, such as o-acetamidobenzoyl. R' denotes hydrogen, alkyl with 1 to 4 carbon atoms, preferably methyl or ethyl, substituted alkyl with 1 to 4 carbon atoms, for example alkyl halide with 1 to 4 carbon atoms, preferably chloromethyl, bromomethyl, chloroethyl or bromoethyl, cyanoalkyl with 1 to 4 carbon atoms in the alkyl moiety, preferably cyanomethyl or cyanoethyl, hydroxyalkyl with 1 to 4 carbon atoms, preferably hydroxymethyl or hydroxyethyl, alkoxyalkyl with 1 to 4 carbon atoms in the alkoxy as well as in the alkyl moiety, preferably methoxymethyl, ethoxymethyl or methoxyethyl, ω-carboxy-ω-aminoalkyl with 1 to 4 carbon atoms in the alkyl moiety, preferably ω-carboxy-ω-aminopropyl, ω-carboxy-ω-acylaminoalkyl with 1 to 4 carbon atoms in the alkyl moiety and 1 to 7 carbon atoms in the acyl moiety, preferably ω-carboxy-ω-benzoyl-aminopropyl, ω-carboxyalkyl with 1 to 4 carbon atoms in the alkyl moiety, preferably carboxymethyl or carboxyethyl a possibly substituted, saturated or singly or multiply unsaturated, 5- to 7-membered carbocyclic ring, for example cycloalkyl, preferably cyclohexyl, cycloalkenyl, preferably cyclohexenyl, cycloalkadienyl, preferably cyclohexadienyl, possibly substituted aryl or aryloxy of the formulae

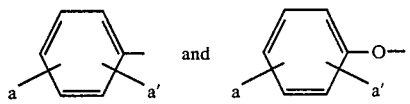

in which a and a' are identical or different and denote hydrogen, $C_1$–$C_4$-alkyl, preferably methyl or ethyl, hydroxy, $C_1$–$C_4$ alkoxy, preferably methoxy or ethoxy, $C_1$–$C_4$-acyloxy, preferably acetoxy, halogen, preferably fluorine and chlorine, carboxy, sulfoxy, amino, $C_1$–$C_4$-acylamino, preferably acetamino, R' may also denote optionally substituted 5 or 6-membered heteroaryl containing nitrogen, sulfur or oxygen as heteroatoms, for example 2-pyridon-1-yl, 4-pyridon-1-yl, 3,5-dichloro-4-pyridon-1-yl, 2-thienyl, 1-tetrazolyl, preferably 2-furyl, 2-thienyl or 1-tetrazolyl. R' may also stand for an optionally substituted, 5- or 6-membered heteroarylthio radical which may contain nitrogen, sulfur or oxygen, as heters atoms in the ring, such as preferably 2-methyl-1,3,4-thiadiazol-5-yl-thio or 2- amino-1,3,4-thiadiazol-5-yl-thio. R'' and R''', which are identical or different, may be hydrogen, alkyl with 1 to 4 carbon atoms, preferably methyl, hydroxy, optionally substituted acyloxy with 1 to 4 carbon atoms in the acyl moiety, for example formyloxy, acetoxy, propionyloxy, optionally substituted alkoxy with 1 to 4 carbon atoms in the alkyl moiety, for example methoxy, ethoxy, propoxy, amino, optionally substituted alkyl amino with 1 to 6 carbon atoms in the alkyl moiety, such as preferably tert. butylamino, tert. amylamino, benzylamino, p-methoxybenzylamino, benzhydrylamino, tritylamino, phenylethylamino, optionally substituted acyl amino, for example formamido, acetylamino, chloroacetylamino, bromoacetylamino, benzoylamino, tert. butoxycarbonylamino, 2,2,2-trichloroethoxycarbonylamino, 4-hydroxy-1,5-naphthyridin-3-carbonylamino, 3-hydroxy-pyridazin-4-carbonylamino, imidazolidin-2-on-1-yl-carbonylamino, (3-methyl-sulfonyl-imidazolidin-2-on-1-yl)-carbonylamino, (4-ethyl-piperazin-2,3-dion-1-yl)-carbonylamino, alkoxycarbonyl with 1 to 4 carbon atoms in the alkyl moiety, for example methoxycarbonyl, ethoxy-carbonyl, halogen, preferably chlorine and bromine, cyano, sulfoxy or aminosulfonyl.

In the radical X of the formula

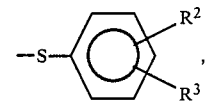

$R^2$ may especially stand for a nitro group in para- or ortho-position o sulfur and $R^3$ for hydrogen, a nitro group, halogen, alkyl with 1 to 4 carbon atoms, such as preferably methyl, ethyl, n-propyl, i-propyl, n-butyl and tertiary butyl, for cyano, carboxy, for alkoxycarbonyl with 1 to 4 carbon atoms in the alkyl moiety, such as preferably methoxycarbonyl and ethoxycarbonyl and for aminocarbonyl.

X preferably means p-nitrophenylthio, o-nitrophenylthio, o,p-nitrophenylthio, m-carboxy-p-nitrophenylthio, m-cyano-p-nitrophenylthio, o-cyano-p-nitrophenylthio, p-carboxy-o-nitrophenylthio and p-cyano-o-nitrophenylthio.

A further feature of the present invention is a process for the manufacture of cephalosporins of the formula I, which comprises reacting a compound of the formula III

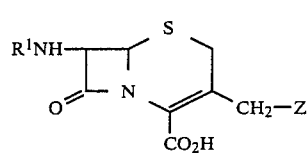

in which Z means formyloxy, acetoxy, acetoacetoxy or amino- carbonyloxy, and $R^1$ has the above-mentioned meaning, with a compound of the formula H—X, wherein X has the above-mentioned meaning, and in the case of $R^1$ being hydrogen, reacting it with formic acid, an optionally substituted arylcarboxylic acid or a carboxylic acid of the formula IV

or a reactive derivative thereof.

The starting compounds required for carrying out the process of the invention are known from the literature or can be prepared by processes described in literature.

The reaction of compound III with compounds of the formula H—X is suitably carried out in an aqueous medium, with addition of organic solvents miscible with water, such as preferably methanol, ethanol, isopropanol, acetonitrile, acetone, dimethyl formamide, dimethyl acetamide, tetrahydrofuran or dioxan, to improve the solubility of the components of the reaction.

The compound of the formula H—X can also be used in the form of a salt, for example an alkali metal or alkaline earth metal salt, especially a sodium or potassium salt or a salt with an optionally substituted ammonium cation.

The reaction components are reacted in any ratio, but preferably in a molar ratio to an about 5-molar ratio.

The temperature of the reaction is not critical, but it should preferably be about 20° to 80° C. It may be advantageous to add to the reaction mixture an organic solvent boiling at the desired reaction temperature, which solvent is soluble or insoluble in water, thus maintaining a constant reaction temperature.

During the reaction of pH of the reaction mixture is kept in a range of about 5–8, preferably 6.5–7.5, by addition of an acid or base.

According to another variant of the process the compounds of the invention can be prepared by reacting a cephalosporin of formula I, wherein $R^1$ is hydrogen and Z has the above-mentioned meaning, with formic acid, an optionally substituted arylcarboxylic acid or a carboxylic acid of formula

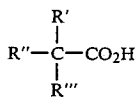      IV in which R', R" and R"' are as defined above or with an activated derivative of said carboxylic acid.

Suitable activated derivatives are, in the first place, the halides, preferably chlorides and bromides, furthermore anhydrides and mixed anhydrides, azides and activated esters, preferably those with p-nitrophenol, 2,4-dinitrophenol, methylene cyanohydrin, N-hydroxysuccinimide and N-hydroxy-phthalimide, more preferably 1-hydroxybenzotriazole and 6-chloro-1-H-hydroxybenzotriazole. Suitable mixed anhydrides are preferably those with lower alkanoic acids, for example acetic acid and more preferably with substituted acetic acids for example trichloroacetic acid, pivalic acid, or cyanoacetic acid. Especially preferred are also mixed anhydrides with carbonic acid semiesters as are obtained, for example, by reacting the carboxylic acids of the formula IV with chloroformic acid benzyl ester, p-nitrobenzyl ester, isobutyl ester, ethyl ester or allyl ester. The activated derivatives can be reacted in the form of isolated substances or in situ. In general, the cephem derivatives of the formula I in which $R^1$ hydrogen are reacted with the carboxylic acid of the formula IV or an activated derivative thereof in the presence of an inert solvent. Especially suitable inert solvents are chlorinated hydrocarbons, preferably methylene chloride and chloroform; ethers, for example diethyl ether, diisopropyl ether and more preferably tetrahydrofurane and dioxane; ketones, preferably acetone and butanone; amides, preferably dimethyl formamide and dimethyl acetamide; or water. It may prove advantageous to use mixtures of the said solvents. This is often the case of the reaction of a cephem compound of the formula I in which $R^1$ is hydrogen with an activated derivative of the carboxylic acid of the formula IV produced in situ.

The reaction of cephem compounds of the formula I in which $R^1$ denotes hydrogen with carboxylic acids of the formula IV or the activated derivatives thereof can be carried out at a temperature in the range from about −50 to about +80° C., preferably −20° to +50° C. and more preferably −20° C. to room temperature.

The time of reaction depends on the reactants used, the temperature and the solvent or solvent mixture used and normally it is in the range from about 15 minutes to about 72 hours.

The reaction of activated derivatives of the carboxylic acids with cephem compounds of the formula I in which $R^1$ is hydrogen is preferably carried out in an alkaline medium at a pH above 7. To this end a base is added to the reaction mixture, preferably potassium or sodium carbonate, potassium or sodium bicarbonate, potassium or sodium hydroxide, pyridine or a trialkyl amine, for example triethyl amine, N-methyl-morpholine, ethyl diisopropyl amine, or potassium tert. butylate.

Upon completion of the reaction, the compounds of formula I according to the invention can be isolated by distillation of the organic solvents added upon complete reaction, by extracting the aqueous phase with ethylacetate or another suitable solvent for removing, for example, non-reacted exchange components of the formula H—X, and by subsequently acidifying the aqueous phase to a pH of 2 to 4, preferably 3, thus precipitating the compounds I and separating them, for example by filtration.

In another variant of the process for isolating the compounds of the invention, the aqueous phase can be extracted at a pH of 2 to 4, preferably 3, with a water-immiscible solvent, such as preferably ethyl acetate. After concentration of the extract in vacuo, the reaction products are precipitated by addition of an organic solvent in which they are barely soluble, for example in ether or petroleum ether.

In a further variant of the process according to the invention, the reaction products of formula I can also be directly extracted from the reaction batch into a water-immiscible organic solvent, such as preferably ethyl acetate, at a higher pH than pH 4. The further work up is carried out as described above.

Besides the compounds specified in the examples, the following compounds of formula I can, for example, also be prepared by the process of the invention.

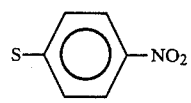

-continued

| R¹ | X | R¹ | X |
|---|---|---|---|
| CH₃CO | 2-nitrophenyl-S- | C₆H₅OCH₂CO | " |
| HCO | " | | |
| C₆H₅CO | " | HCO | 2-nitro-3-cyanophenyl-S- (5-S-2-NO₂-3-CN-C₆H₃) |
| C₆H₅CH₂CO | " | CH₃CO | " |
| C₆H₅OCH₂CO | " | C₆H₅CO | " |
| 2-thienyl-CH₂CO | " | C₆H₅CH₂CO | " |
| | | C₆H₅OCH₂CO | 3-cyano-4-nitrophenyl-S- |
| | | 2-thienyl-CH₂CO | " |
| HCO | 2,4-dinitrophenyl-S- | | |
| CH₃CO | " | HCO | 2-cyano-4-nitrophenyl-S- |
| | | CH₃CO | " |
| C₆H₅CO | " | C₆H₅CO | " |
| C₆H₅CH₂CO | " | C₆H₅CH₂CO | " |
| C₆H₅OCH₂CO | " | C₆H₅OCH₂CO | " |
| 2-thienyl-CH₂CO | " | 2-thienyl-CH₂CO | " |
| HCO | 4-carboxy-2-nitrophenyl-S- | CH₃CO | 4-cyano-3-nitrophenyl-S- |
| CH₃CO | " | C₆H₅CO | " |
| C₆H₅CO | " | C₆H₅CH₂CO | " |
| C₆H₅CH₂CO | " | | |
| C₆H₅OCH₂CO | " | | |

-continued

| R¹ | X | R¹ | X |
|---|---|---|---|
| 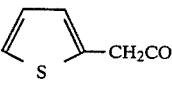 | " | C₆H₅OCH₂CO | " |
| HCO |  | 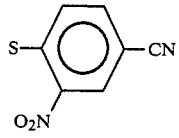 | " |
| 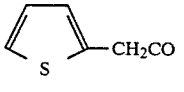 | 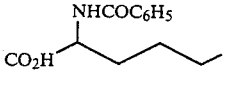 | 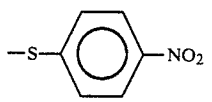 | 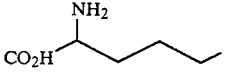 |
| " | 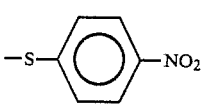 | " | 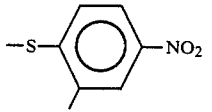 |
| " | 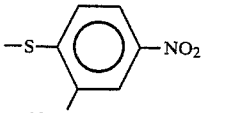 | " | 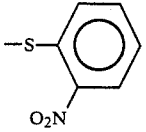 |
| " | 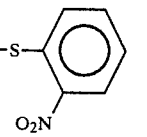 | " | 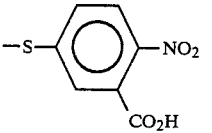 |
| " | 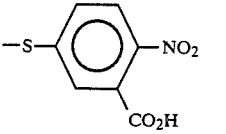 | " | 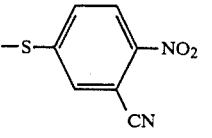 |
| " | 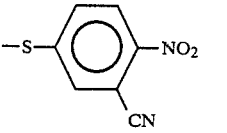 | " | 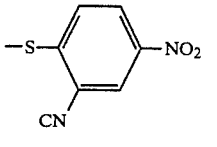 |
| 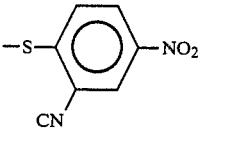 | 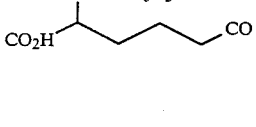 | 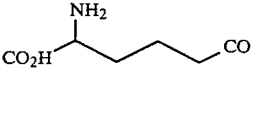 | 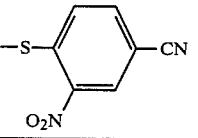 |
| " | 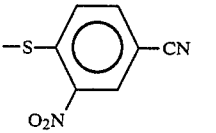 | " | 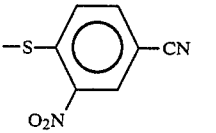 |

The examples illustrate the invention without implying a limitation of the subject of the invention.

7-β-thieno-2-yl-acetamido-3-[(4-nitro-3-carboxyphenyl)-thiomethyl]-3-cephem-4-carboxylic acid, especially suitable for the general detection of β-lactamases, is slightly yellow λ$_{max}$344 nm) in buffered solutions (pH of 7.3). After reaction with a β-lactamase, for example the enzyme of Enterobacter cloacae P 99, the yellow color λ$_{max}$405 nm) characteristic of p-nitrothiophenolates occurs. The intensity of the color of course depends on the pH of the solution and has its maximum at a pH of 8.0. For routine analysis, however, pH 7.3 can be considered as sufficient. The maximum extinction difference utilizable between substrate and reaction product occurs at 415 nm. An analogous reaction of this preferred compounds takes place also with other β-lactamases, for example from *Escherichia coli* $R_{TEM}$, *Klebsiella aerogenes* 1082 E, *Pseudomonas aeruginosa* 18 SH, *Bacteroides fragilis* 620 and *Staph. aureus* R 85. Other chromogenic cephalosporins according to the invention exhibit a corresponding change in color in the reaction with β-lactamases.

The compounds according to the invention can also be used for the detection of β-lactamases by directly adding, for example, isolated β-lactamases or cell suspensions of germs producing β-lactamases, to neutrally buffered aqueous solutions of the chromogenic cephalosporins, so that, when using an appropriate concentration of the chromogenic cephalosporin, the characteristic change in color is observed.

Alternatively, clinical isolates obtained in a different manner can be spread in the form of a colony smear on a wetted test strip of paper or another suitable carrier material, for example absorbent plastic material, dextrans or other natural polymers, which had previously been impregnated with appropriate, preferably aqueous, solutions of the compounds of the invention. In this case, too, the characteristic change in color can be observed within a short period of time.

Moreover, the compounds according to the invention can be used for purification of β-lactamases in order to ascertain, for example, the position of the β-lactamase peak in column chromatography separation processes. Another advantageous use of the compounds according to the invention is provided in the enzyme-kinetic analysis for the determination of β-lactamase inhibitors, for example clavulanic acid, which partly or totally impede the reaction of a suitable β-lactamase with the compounds according to the invention.

EXAMPLE 1

7-β-thien-2-yl-acetamido-3-[(4-nitrophenyl)-thiomethyl]-3-cephem-4-carboxylic acid 2 g of p-nitrothiophenol were stirred at 64° C. for 2 hours with 4.2 g of sodium salt of 7-thien-2-yl-acetamido-cephalosporanic acid in 120 ml of acetone/water (1/1) at pH 6.5 to 7.2. After addition of another 0.5 g of p-nitrothiophenol, stirring was continued for another 2 hours. After cooling to room temperature, the product was adjusted to pH 7.0 with 2N hydrochloric acid, extracted twice with ethyl acetate, ethyl acetate residues were removed from the aqueous phase on a rotary evaporator, and the aqueous phase was acidified at 0° C. with 2N hydrochloric acid to pH 2.0. There was obtained a clear yellow precipitate which was suction filtered and dried in vacuo over phosphorus pentoxide. 3.2 g of the title compound were obtained. NMR (DMSO-$d_6$):
$\delta = 6.9$–7.5 ppm (thienyl, 3H)
$\delta = 4.2$ ppm (s, 2H, $CH_2$—CO)
$\delta = 9.0$ ppm (d, 1H, CONH)
$\delta = 5.6$ ppm (q, 1H, C—7—H)
$\delta = 5.1$ ppm (d, 1H, C—6—H)
$\delta = 3.8$ ppm (S, 2H, C—2—$CH_2$) 3.6 (AB, 2H $CH_2$—S)
$\delta = 7.5$ ppm (4H, p-disubst.-phenyl) 8.1

EXAMPLE 2

7-β-phenylacetamido-3-[(4-nitro-3-carboxyphenyl)-thiomethyl]-3-cephem-4-carboxylic acid 1.95 g of 7-phenylacetamido-cephalosporanic acid are dissolved under nitrogen in 100 ml of water by addition of sodium bicarbonate at a pH of 7.0. A solution of 6.2 mols of disodium salt of 5-mercapto-2-nitrobenzoic acid in 12 ml of water is added dropwise. Stirring of the mixture is continued at pH 6.5 to 7.2 at room temperature for 1 hour and subsequently for 4 hours at 60° C. After addition of another 3.8 mmols of disodium salt of 5-mercapto-2-nitro-benzoic acid in water, stirring was continued for another 5 hours at 60° C. the batch was cooled and adjusted to a pH of 5.0, and extracted three times with 100 ml portions of ethyl acetate. The aqueous phase was freed from ethyl acetate residues and acidified in an ice bath to pH 2.0. The precipitate was separated and dried in vacuo at 40° C. over phosphorus pentoxide. 2.6 g of the title compound were obtained. MP: 98°–110° C. (Decomp.) NMR (DMSO-$s_6$):
$\delta = 9.1$–9.0 ppm (d, 1H, CONH)
$\delta = 8.1$–7.0 ppm (m, 3H, arom. protons)
$\delta = 7.4$ ppm (s, 5H, phenyl)
$\delta = 5.7$ ppm (q, 1H, C-7-H)
$\delta = 5.2$ ppm (d, 1H, C-6-H)
$\delta = 4.4$ ppm (s, 2H, $CH_2$—S)
$\delta = 3.5$ ppm (s, 4H, $CH_2$CO and C-2-$CH_2$)

EXAMPLE 3

7-β-thien-2-yl-acetamido-3-[(4-nitro-3-carboxyphenyl)-thio-methyl]-3-cephem-4-carboxylic acid 16.7 g of sodium salt of 7-thien-2-yl-acetamido-cephalosporanic acid were dissolved in 650 ml of water and stirred under nitrogen. 50 mmols of disodium salt of 5-mercapto-2-nitrobenzoic acid in 100 ml of water were slowly added dropwise while maintaining the pH at 7.0. At pH 6.9 to 7.1 the batch was heated to 60° C. during 6 hours and subsequently left in the refrigerator. The pH was adjusted to 5.0 and the solution was extracted three times with 200 ml each of ethyl acetate. The aqueous phase was liberated from ethyl acetate residues, cooled to 0° C. and acidified to pH 2 with 2N hydrochloric acid. The precipitate was dried over phosphorus pentoxide. 22 g of the title compound were obtained MP: 99°–104° C. (Decomp.) NMR (DMSO-$d_6$):
$\delta = 9.0$–9.2 ppm (d, 1H, CONH)
$\delta = 7.1$–8.1 ppm (m, arom. protons)
$\delta = 6.8$–7.0 ppm (m, 2H, thienyl 3H, +4H
$\delta = 5.6$-ppm (q, 1H, C-7-H)
$\delta = 5.1$ ppm (d, 1H, C-6-H)
$\delta = 4.3$ ppm (s, 2H, $CH_2$—S)
$\delta = 4.8$ ppm (s, 2H, $CH_2$CO)
$\delta = 4.5$ ppm (AB, 2H, C-2-$CH_2$)

Example 4

7-β-amino-3[(4-nitro-3-carboxyphenyl)-thiomethyl]-3-cephem-4-carboxylic acid 2.2 g of 7-amino-cephalosphoranic acid were dissolved under nitrogen in 150 ml of water at pH 7.0 with sodium bicarbonate.

10 mmols of disodium salt of 5-mercapto-2-nitrobenzoic acid in 20 ml of water were added dropwise at pH 6.8 to 7.3. Stirring was continued for 1 hour at room temperature and for 6 hours at 60° C., while maintaining the pH at 6.8 to 7.0. The batch was cooled to room temperature, adjusted to a pH of 5.0 with 2N hydrochloric acid, and extracted three times with 50 ml portions of ethyl acetate. The aqueous phase was freed from ethyl acetate residues, cooled to 0° C. and acidified to pH 2.0. The product was suction-filtered and dried. The yield was 2.4 g of the title compound. MP: 230° C. (Decomp.) NMR (DMSO-$d_6$)
δ=8.1–7.5 ppm (m, arom. protons)
δ=5.1 ppm (d, 1H, C-7-H)
δ=4.8 ppm (d, 1H, C-6-H)
δ=4.3 ppm (d, 2H, $CH_2$—S)
δ=3.6 ppm (AB, 2H, C-2-$CH_2$)

EXAMPLE 5

7-β-phenylacetamido-3-[(4nitro-3-carboxyphenyl)-thiomethyl]-3-cephem-4-carboxylic acid 822 mg of 7-amino-3-[(4-nitro-3-carboxyphenyl)-thiomethyl]-3-cephem-4-carboxylic acid are dissolved in 200 ml of water with 500 mg of sodium bicarbonate, 20 ml of acetone are added, and the batch is cooled to 0° C. to 5° C. in an ice bath. 350 mg of phenacetyl chloride in 5 ml of acetone are added dropwise and with agitation. After 30 minutes of stirring another 50 mg of phenacetyl chloride in 2 ml of acetone are added. After ½ hour the acetone is removed and the aqueous phase is acidified with 2N hydrochloric acid to pH 20. The precipitate is collected, washed with water and dried. 750 mg of the title compound with physical properties identical to those of the compound obtained according to Example 2 are isolated.

EXAMPLE 6

7-β-thien-2-yl-acetamido-3-[(4-nitro-3-carboxyphenyl)-thio-methyl]-3-cephem-4-carboxylic acid Proceeding as in Example 5, but using a total of 415 mg of thien-2-yl-acetyl chloride instead of phenacetyl chloride, 670 mg of the title compound with physical properties identical to those of the compound obtained according to Example 3 are isolated.

What is claimed is:
1. 7-β-thien-2-yl-acetamido-3-[(4-nitro-carboxyphenyl)-thiomethyl]-3-cephem-4-carboxylic acid.

* * * * *